US008449453B2

(12) United States Patent
Fujimoto et al.

(10) Patent No.: US 8,449,453 B2
(45) Date of Patent: May 28, 2013

(54) ENDOSCOPIC IMAGE PROCESSING APPARATUS AND ENDOSCOPE SYSTEM

(75) Inventors: Takehide Fujimoto, Tokyo (JP); Kiyotaka Kanno, Higashimurayama (JP); Tatsuhiko Suzuki, Hino (JP); Hidekazu Shinano, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 4 days.

(21) Appl. No.: 13/341,250

(22) Filed: Dec. 30, 2011

(65) Prior Publication Data

US 2012/0178992 A1 Jul. 12, 2012

Related U.S. Application Data

(63) Continuation of application No. PCT/JP2011/063696, filed on Jun. 15, 2011.

(30) Foreign Application Priority Data

Jul. 12, 2010 (JP) ................................ 2010-158302

(51) Int. Cl.
*A61B 1/04* (2006.01)
*H04N 5/08* (2006.01)
*A61B 1/00* (2006.01)
(52) U.S. Cl.
CPC .................................. *A61B 1/00009* (2013.01)
USPC .............. 600/109; 600/118; 348/74; 348/525
(58) Field of Classification Search
CPC .......................... A61B 1/00006; A61B 1/00009
USPC ................... 600/109, 110, 117, 118; 348/65, 348/74, 76, 518, 525
See application file for complete search history.

(56) References Cited

U.S. PATENT DOCUMENTS

| 4,831,444 | A | * | 5/1989 | Kato | 348/518 |
| 5,434,615 | A | * | 7/1995 | Matumoto | 348/72 |
| 5,585,840 | A | * | 12/1996 | Watanabe et al. | 348/65 |
| 6,449,007 | B1 | * | 9/2002 | Yokoyama | 348/73 |

(Continued)

FOREIGN PATENT DOCUMENTS

| JP | 04-156072 | 5/1992 |
| JP | 2001-275954 | 10/2001 |
| JP | 2008-036356 | 2/2008 |

OTHER PUBLICATIONS

Japanese Search Report dated Aug. 9, 2011 issued in PCT/JP2011/063696.

*Primary Examiner* — John P Leubecker
(74) *Attorney, Agent, or Firm* — Scully, Scott, Murphy & Presser, P.C.

(57) ABSTRACT

An endoscopic image processing apparatus includes an endoscope information reading section that reads endoscope information that is information relating to an endoscope from the endoscope, a synchronizing signal detecting section that is given an image pickup signal that includes a synchronizing signal outputted by an image pickup device provided in the endoscope from the endoscope, performs detection processing of the synchronizing signal, outputs the detected synchronizing signal when the synchronizing signal can be detected, and generates and outputs a synchronizing signal based on the endoscope information read by the endoscope information reading section when the synchronizing signal cannot be detected, and an image signal generating section that generates an image signal based on the synchronizing signal outputted from the synchronizing signal detecting section and the image pickup signal outputted from the image pickup device of the endoscope.

12 Claims, 5 Drawing Sheets

U.S. PATENT DOCUMENTS

| | | | |
|---|---|---|---|
| 7,355,625 B1 * | 4/2008 | Mochida et al. | 348/65 |
| 7,704,204 B2 * | 4/2010 | Shigemori et al. | 600/109 |
| 7,804,523 B2 * | 9/2010 | Ikeda et al. | 348/222.1 |
| 2004/0073086 A1 * | 4/2004 | Abe | 600/109 |
| 2005/0018042 A1 * | 1/2005 | Rovegno | 348/65 |
| 2008/0039686 A1 | 2/2008 | Mori et al. | |
| 2009/0051762 A1 * | 2/2009 | Shigemori et al. | 348/65 |
| 2011/0013037 A1 * | 1/2011 | Irikura et al. | 348/222.1 |

* cited by examiner

ENDOSCOPIC IMAGE PROCESSING
APPARATUS AND ENDOSCOPE SYSTEM

CROSS REFERENCE TO RELATED
APPLICATION

This application is a continuation application of PCT/JP2011/063696 filed on Jun. 15, 2011 and claims benefit of Japanese Application No. 2010-158302 filed in Japan on Jul. 12, 2010, the entire contents of which are incorporated herein by this reference.

BACKGROUND OF THE INVENTION

1. Field of the Invention

The present invention relates to an endoscopic image processing apparatus that processes an endoscopic image from an image pickup device, and an endoscope system.

2. Description of the Related Art

In recent years, endoscopes have been widely used in diagnosis, treatment using treatment instruments and the like in a medical field. An electronic endoscope apparatus has come into widespread use which is provided with an image pickup device such as a charge coupled device (CCD) at a distal end of an endoscope insertion portion, and projects an observation image picked up with use of the CCD on a television monitor by a video processor.

The video processor is provided with a drive circuit, so that a drive signal from the drive circuit is transmitted to the CCD at an endoscope distal end to drive the CCD. In the drive circuits like this, some drive circuits supply drive signals with synchronizing signals (VD) superimposed on the drive signals to CCDs. The CCDs output video signals of each pixel synchronously with the synchronizing signals.

A synchronizing signal (VD) is superimposed on the video signal from a CCD. The video processor extracts the synchronizing signal included in the video signal from the CCD, and uses the synchronizing signal in the following video processing. Japanese Patent Application Laid-Open Publication No. 4-156072 discloses a head detachable camera in which a phase shift is compensated irrespective of a delay of the transmission path from the CCD to the video processor.

Various endoscopes having different kinds of transmission paths connecting CCDs and the video processor, different kinds of CCDs, and the like can be connected to the video processor.

SUMMARY OF THE INVENTION

An endoscopic image processing apparatus according to the present invention includes an endoscope information reading section that reads endoscope information that is information relating to an endoscope from the endoscope, a synchronizing signal detecting section that is given an image pickup signal that includes a synchronizing signal outputted by an image pickup device provided in the endoscope from the endoscope, performs detection processing of the synchronizing signal, outputs the detected synchronizing signal when the synchronizing signal can be detected, and generates and outputs a synchronizing signal based on the endoscope information read by the endoscope information reading section when the synchronizing signal cannot be detected, and an image signal generating section that generates an image signal based on the synchronizing signal outputted from the synchronizing signal detecting section and the image pickup signal outputted from the image pickup device of the endoscope.

Further, an endoscope system according to the present invention is an endoscope system including an endoscope and a video processor connected to the endoscope, in which the endoscope includes an image pickup device that picks up an image of a subject, and outputs an image pickup signal including a synchronizing signal, a storing section that stores endoscope information that is information relating to the endoscope, and the video processor includes an endoscope information reading section that reads the endoscope information from the endoscope, a synchronizing signal detecting section that is given an image pickup signal that includes a synchronizing signal outputted by the image pickup device from the endoscope, performs detection processing of the synchronizing signal, outputs the detected synchronizing signal when the synchronizing signal can be detected, and generates and outputs a synchronizing signal based on the endoscope information read by the endoscope information reading section when the synchronizing signal cannot be detected, and an image signal generating section that generates an image signal based on the synchronizing signal outputted from the synchronizing signal detecting section and the image pickup signal outputted from the image pickup device of the endoscope.

DETAILED DESCRIPTION OF THE PREFERRED
EMBODIMENT

Hereinafter, an embodiment of the present invention will be described in detail with reference to the drawings.

Figure 1:
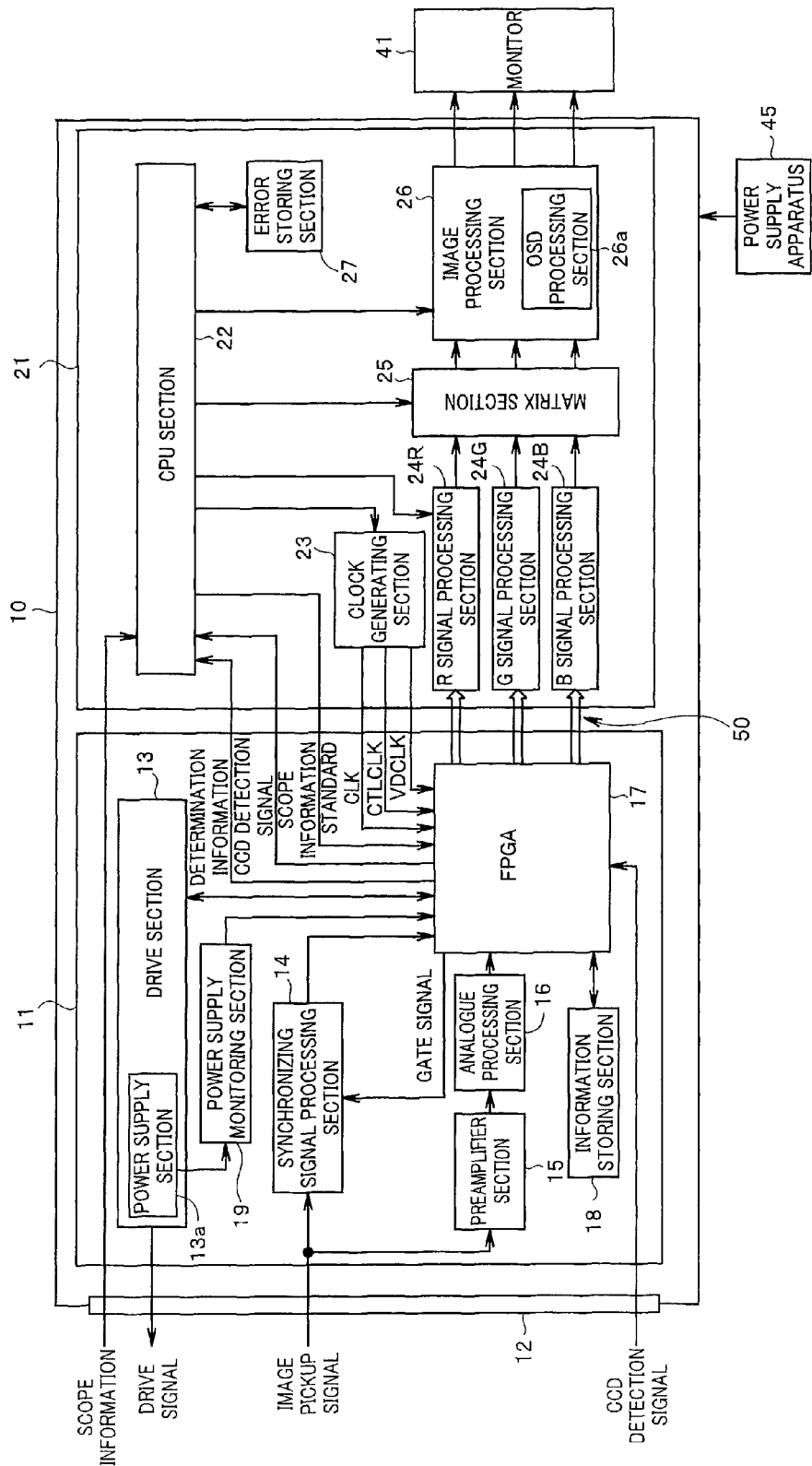
FIG. 1 is a block diagram showing an endoscopic image processing apparatus according to one embodiment of the present invention.

FIG. 1 is a block diagram showing an endoscopic image processing apparatus according to one embodiment of the present invention. Further, FIG. 2 is an explanatory view showing an endoscope system in which the endoscopic image processing apparatus is incorporated.

Figure 2:
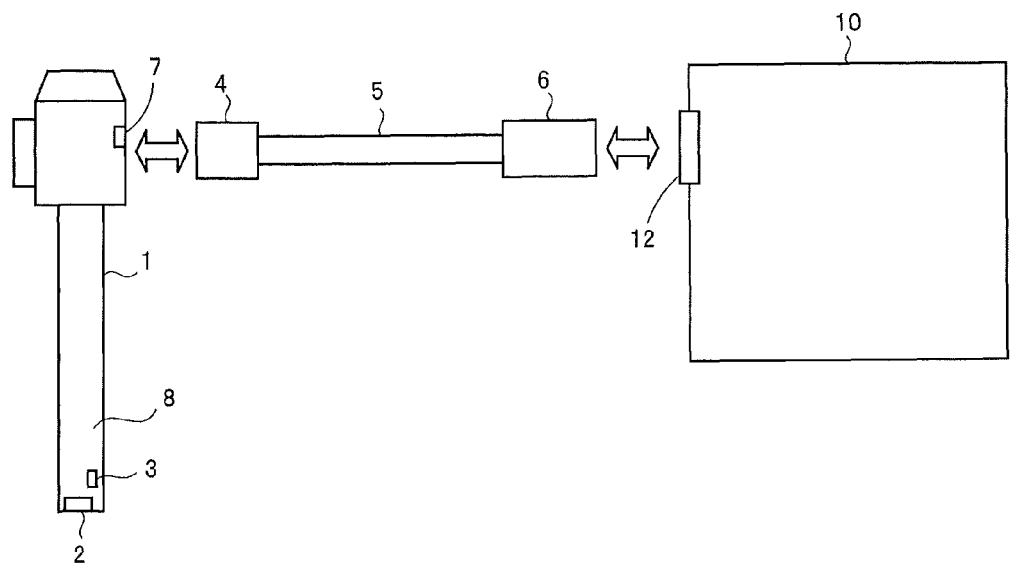
FIG. 2 is an explanatory view showing an endoscope system in which the endoscopic image processing apparatus is incorporated.

The endoscope system shown in FIG. 2 is configured by a scope 1 and a video processor 10 being connected by a scope cable 5. The scope 1, which is an endoscope, has an elongated insertion portion 8 having flexibility, and has a CCD 2 as a solid image pickup device incorporated in a distal end side of the insertion portion 8. Further, the scope 1 is provided with a ROM 3 in which scope information such as information relating to the scope 1, and information relating to a scope cable length, for example, is written. The scope information which is stored in the ROM 3 includes information of the scope 1 and the cable length of the scope cable 5.

The scope 1 and the scope cable 5 are attachably and detachably connected by a connector 4, and the scope cable 5 and the video processor 10 are attachably and detachably connected by connectors 6 and 12.

As shown in FIG. 1, the video processor 10 is configured by a patient circuit 11 and a secondary circuit 21 which are insulated from each other. The patient circuit 11 is provided with a drive section 13, and the drive section 13 generates a drive signal for driving the CCD 2 based on a timing signal or the like from an FPGA (Field Programmable Gate Array) 17 which will be described later. Further, power supply to the scope 1 is performed by the drive section 13.

The drive section 13 needs to generate a drive signal corresponding to the kind of the CCD 2 incorporated in the scope 1, and the kind of the CCD 2 needs to be grasped in the video processor 10 side. The scope 1 is provided with a detection resistor 7 for detecting the kind of the CCD like this. The connector 6 of the scope cable 5 and the connector 12 of the video processor 10 are connected, whereby a CCD detection signal based on the resistance value of the detection resistor 7 is supplied to the FPGA 17. The FPGA 17 supplies the CCD detection signal to a CPU section 22 of the secondary circuit 21.

The CPU section 22 controls a clock generating section 23 to cause the clock generating section 23 to generate a reference clock (reference CLK) of the frequency corresponding to the CCD detection signal. Further, the clock generating section 23 generates a control clock (hereinafter, abbreviated as CTLCLK) for causing the FPGA 17 to detect the CCD, and a synchronizing clock (hereinafter, abbreviated as VDCLK) for generating a synchronizing signal and supplies the control clock and the synchronizing clock to the FPGA 17.

The FPGA 17 generates a timing signal including various clocks necessary for drive of the CCD 2 by using the reference CLK from the clock generating section 23 and gives the timing signal to the drive section 13. Further, the FPGA 17 gives the VDCLK from the clock generating section 23 to the drive section 13. With use of the timing signal from the FPGA 17, the drive section 13 generates a drive signal for the CCD 2, and superimposes a synchronizing signal (VD) on the drive signal to output the drive signal.

The FPGA 17 stops supply of the timing signal to the drive section 13, and stops supply of power to the scope 1, when detecting that the CCD which cannot be driven is connected thereto by the CCD detection signal. Further, the FPGA 17 outputs determination information indicating that the CCD which cannot be driven is connected, to the CPU section 22. The CPU section 22 causes an error storing section 27 to store the determination information.

In order to drive the CCD 2, a plurality of voltages of, for example, 5, 7, 10, 13 and 15 V and the like are necessary, a power supply section 13a of the drive section 13 can generate a plurality of voltages based on a power supply control signal from the FPGA 17 by using a power supply voltage from a power supply apparatus 45.

In this case, the FPGA 17 can generate a power supply control signal corresponding to the kind of the connected CCD. In the present embodiment, an information storing section 18 stores power supply control information corresponding to the kind of the CCD. The FPGA 17 reads the corresponding power supply control information from the information storing section 18 based on the CCD detection signal, generates a power supply control signal based on the read power supply control information, and generates the voltage corresponding to the kind of the CCD in the sequence corresponding to the kind of the CCD.

Further, the power supply section 13a supplies the generated voltage to the CCD 2, and gives the voltage to a power supply monitoring section 19. The power supply monitoring section 19 converts the voltage generated by the power supply section 13a into a digital signal and feeds back the digital signal to the FPGA 17. Further, the power supply monitoring section 19 detects a current which is supplied to the scope 1 from the power supply section 13a, and outputs the digital value of the detection result to the FPGA 17. The FPGA 17 determines whether or not the voltage designated by the power supply control signal from the power supply section 13a is generated correctly in the designated sequence. When the voltage designated by the power supply control signal is not correctly generated in the designated sequence, the FPGA 17 can stop generation of the voltage by controlling the power supply section 13a.

Further, the FPGA 17 detects an overcurrent of a power supply current from the power supply section 13a from the output of the power supply monitoring section 19, and can stop power supply from the power supply section 13a when detecting an overcurrent. At the time of detection of an overcurrent, the FPGA 17 detects only an overcurrent without detecting a rush current.

The drive signal from the drive section 13 is supplied to the CCD 2 of the scope 1 through the scope cable 5. Based on the drive signal, the CCD 2 photo-electrically converts an optical image from a subject, and transmits an image pickup signal to the video processor 10 through the scope cable 5. More specifically, the CCD 2 has a light from the subject incident on each pixel, accumulates charges corresponding to the incident light amount in each pixel, and outputs the accumulated charges as an image pickup signal by the drive signal from the drive section 13.

The image pickup signal from the CCD 2 has a synchronizing signal superimposed thereon. The CCD 2 superimposes a synchronizing signal on the image pickup signal at timing corresponding to an OB (optical black) section not illustrated of the CCD 2, for example. The image pickup signal from the CCD 2 is supplied to a synchronizing signal processing section 14 and a preamplifier section 15 in the video processor 10.

Figure 3:
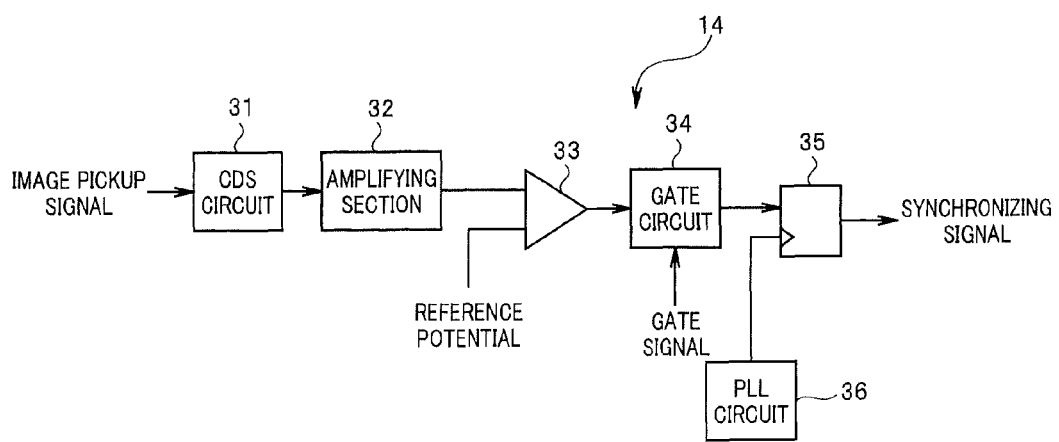
FIG. 3 is a block diagram showing a specific configuration of a synchronizing signal processing section 14 in FIG. 1.

FIG. 3 is a block diagram showing a specific configuration of the synchronizing signal processing section 14 in FIG. 1. The image pickup signal from the CCD 2 is supplied to a CDS circuit (correlated double sampling circuit) 31 of the synchronizing signal processing section 14. The CDS circuit 31 removes a noise included in the image pickup signal, and outputs the image pickup signal to an amplifying section 32. The amplifying section 32 amplifies the image pickup signal, and outputs the image pickup signal to a comparator 33. A predetermined reference potential is also supplied to the comparator 33, and the comparator 33 outputs a timing signal indicating a time period of the image pickup signal at a higher level than the reference potential to a gate circuit 34.

The synchronizing signal is superimposed correspondingly to the OB section, and the level of the synchronizing signal is set to be a level higher than the image pickup signals at other pixel positions in the OB section. Further, in the drive section 13, the synchronizing signal is superimposed on the drive signal by using the timing signal from the FPGA 17, and therefore, the FPGA 17 can predict the position of the synchronizing signal which is superimposed on the image pickup signal, that is, the time period of the image pickup signal corresponding to the OB section. The FPGA 17 predicts the time period in which the synchronizing signal is superimposed, generates a gate signal for separating the synchronizing signal with respect to the image pickup signal near the time period, and gives the gate signal to the gate circuit 34 of the synchronizing signal processing section 14. The gate circuit 34 outputs a timing signal in the time period specified by the gate signal. In the time period specified by the gate signal, the level of the image pickup signal is sufficiently low, and by setting the reference potential to be a level of the synchronizing signal or lower, the synchronizing signal can be separated by the comparator 33 and the gate circuit 34.

A latch circuit 35 outputs the timing signal from the comparator 33 at clock timing from a PLL circuit 36 as the synchronizing signal. The synchronizing signal separated in the synchronizing signal processing section 14 is supplied to the FPGA 17.

Meanwhile, the image pickup signal from the CCD 2 is also supplied to the preamplifier section 15. The preamplifier section 15 amplifies the inputted image pickup signal and supplies the image pickup signal to an analog processing section 16. The analog processing section 16 has a CDS circuit, an A/D convertor and the like not illustrated, and after removing a noise of the inputted image pickup signal, the analog processing section 16 converts the image pickup signal into a digital signal to output the digital signal to the FPGA 17.

The FPGA 17 converts the image pickup signal inputted from the analog processing section 16 into R, G and B video signals, multiplexes a synchronizing signal onto the R, G and B video signals, and transmits the R, G and B video signals to R, G and B signal processing sections 24R, 24G and 24B of a secondary circuit 21 through a plurality of transmission paths 50 by adopting LVDS (low voltage differential signaling).

Figure 4:
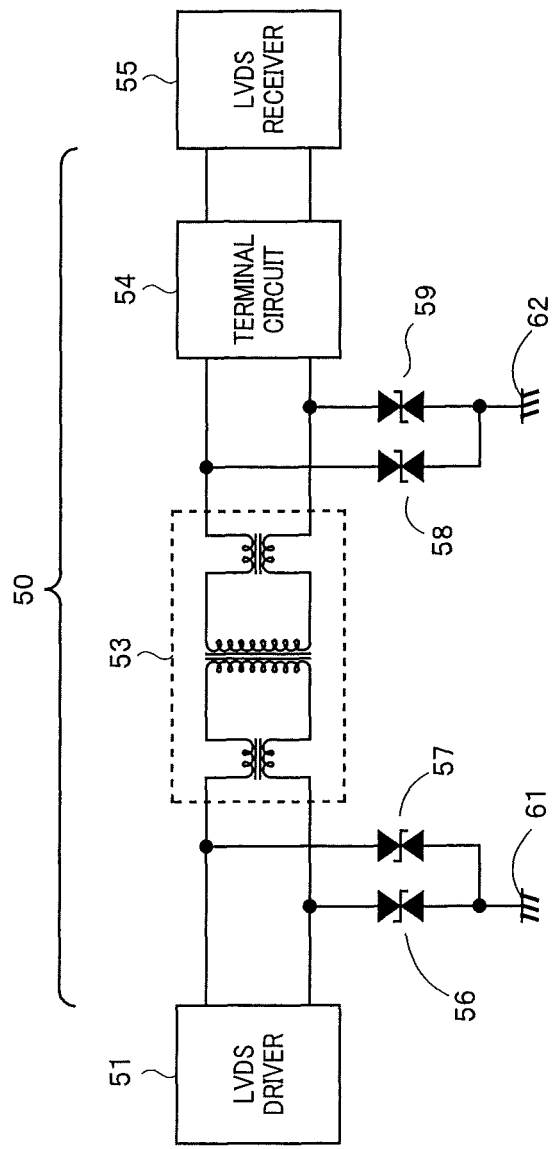
FIG. 4 is a circuit diagram showing a specific configuration of each transmission path 50.

FIG. 4 is a circuit diagram showing a specific configuration of each of the transmission paths 50. The FPGA 17 has LVDS drivers 51 of three systems for the R, G and B video signals, and the R, G and B signal processing sections 24R, 24G and 24B have LVDS receivers 55 respectively.

Each of the transmission paths 50 in an LVDS interface is configured by two lines which respectively transmit data signals with opposite phases from each other as a set (pair). On the signal lines, a pulse transformer section 53 and a terminal circuit 54 are provided.

In the present embodiment, a varistor 56 is connected to between one signal line connected to the LVDS driver 51 and a reference potential point 61 of the patient circuit 11, and a varistor 57 is connected to between the other signal line and the reference potential point 61. Further, a varistor 59 is connected to between one signal line connected to the LVDS receiver 55 and a reference potential point 62 of the secondary circuit 21, and a varistor 58 is connected to between the other signal line and the reference potential point 62.

Each of the circuits of the patient circuit 11 is insulated with respect to the reference potential point 61, and the patient circuit 11 is in an electrically floating state. Therefore, static electricity accumulated in the patient circuit 11 is discharged through a portion with the lowest impedance with respect to the reference potential point 61 in the patient circuit 11. If a device is present on the discharge path, the device is likely to be broken by the discharge.

However, in the present embodiment, in each of the transmission paths 50, the varistors 56 and 57 are provided between a pair of signal lines and the reference potential point 61, and the varistors 58 and 59 are provided between a pair of signal lines and the reference potential point 62. Accordingly, the static electricity accumulated in the patient circuit 11 flows to the reference potential point 62 of the secondary circuit through the varistors 56 to 59.

More specifically, in the present embodiment, devices are not present except for the pulse transformer section 53 on the discharge path of static electricity, and breakage of devices by discharge of static electricity can be prevented.

In the present embodiment, the FPGA 17 determines whether or not a synchronizing signal is normally separated in the synchronizing signal processing section 14, and superimposes the synchronizing signal from the synchronizing signal processing section 14 on the video signal when the synchronizing signal is normally separated, whereas when the synchronizing signal is not normally separated, the FPGA 17 superimposes the synchronizing signal generated based on the data stored in an information storing section 18 on the video signal to output the video signal.

The synchronizing signal which is superimposed on the image pickup signal from the CCD 2 is based on the synchronizing signal outputted by the drive section 13, and can be estimated as being superimposed on the image pickup signal at timing corresponding to a delay time based on the kind of the CCD and the scope cable length. The FPGA 17 generates a synchronizing signal based on the estimation.

In the present embodiment, the information storing section 18 stores information of a delay time based on the information of the kind of the CCD and the scope cable length, that is, the information of the position where the synchronizing signal should be generated as information of the number of counts.

The scope 1 is connected to the video processor 10 through the scope cable 5, whereby the CPU section 22 can read the scope information stored in the ROM 3 of the scope 1. The CPU section 22 outputs the scope information read from the ROM 3 to the FPGA 17. Further, the CCD detection signal is also inputted in the FPGA 17, and the FPGA 17 reads the information of a delay time corresponding to the kind of the CCD and the scope cable length from the information storing section 18 based on the scope information and the CCD detection signal. The FPGA 17 counts the reference CLK by the number of counts based on the information read from the information storing section 18 with the timing signal generated based on the VDCLK as a reference, and thereby, can generate a synchronizing signal.

The R, G and B signal processing sections 24R, 24G and 24B of the secondary circuit 21 receive the R, G and B video signals on which the synchronizing signal is superimposed from the FPGA 17, respectively. The R, G and B signal processing sections 24R, 24G and 24B are controlled by the CPU section 22, apply predetermined color signal processing to the received R, G and B video signals, and thereafter, output the R, G and B video signals to a matrix section 25. The matrix section 25 is controlled by the CPU section 22, applies a predetermined matrix calculation to the inputted R, G and B video signals to generate the R, G and B video signals, and outputs the R, G and B video signals to an image processing section 26. The image processing section 26 is controlled by the CPU section 22, applies γ correction processing and white balance adjustment processing respectively to the inputted R, G and B video signals, and thereafter, outputs the R, G and B video signals to a monitor 41. Further, the image processing section 26 includes an OSD processing section 26a, and the OSD processing section 26a can superimpose a character corresponding to an instruction from the CPU section 22.

Thus, the endoscopic image picked up by the CCD 2 can be displayed on the monitor 41.

When the FPGA 17 determines that the synchronizing signal cannot be normally separated in the synchronizing signal processing section 14, the FPGA 17 supplies the determination information indicating that the synchronizing signal cannot be normally separated in the synchronizing signal processing section 14 to the CPU section 22. When the determination information indicates that the synchronizing signal cannot be normally separated in the synchronizing signal processing section 14, the CPU section 22 controls the OSD processing section 26a to cause the OSD processing section 26a to display the message indicating that the synchronizing signal cannot be normally separated in the synchronizing signal processing section 14. For example, the CPU section 22 causes the OSD processing section 26a to display the message such as "Clean the scope cable contact point, and connect the scope cable again."

Figure 5:
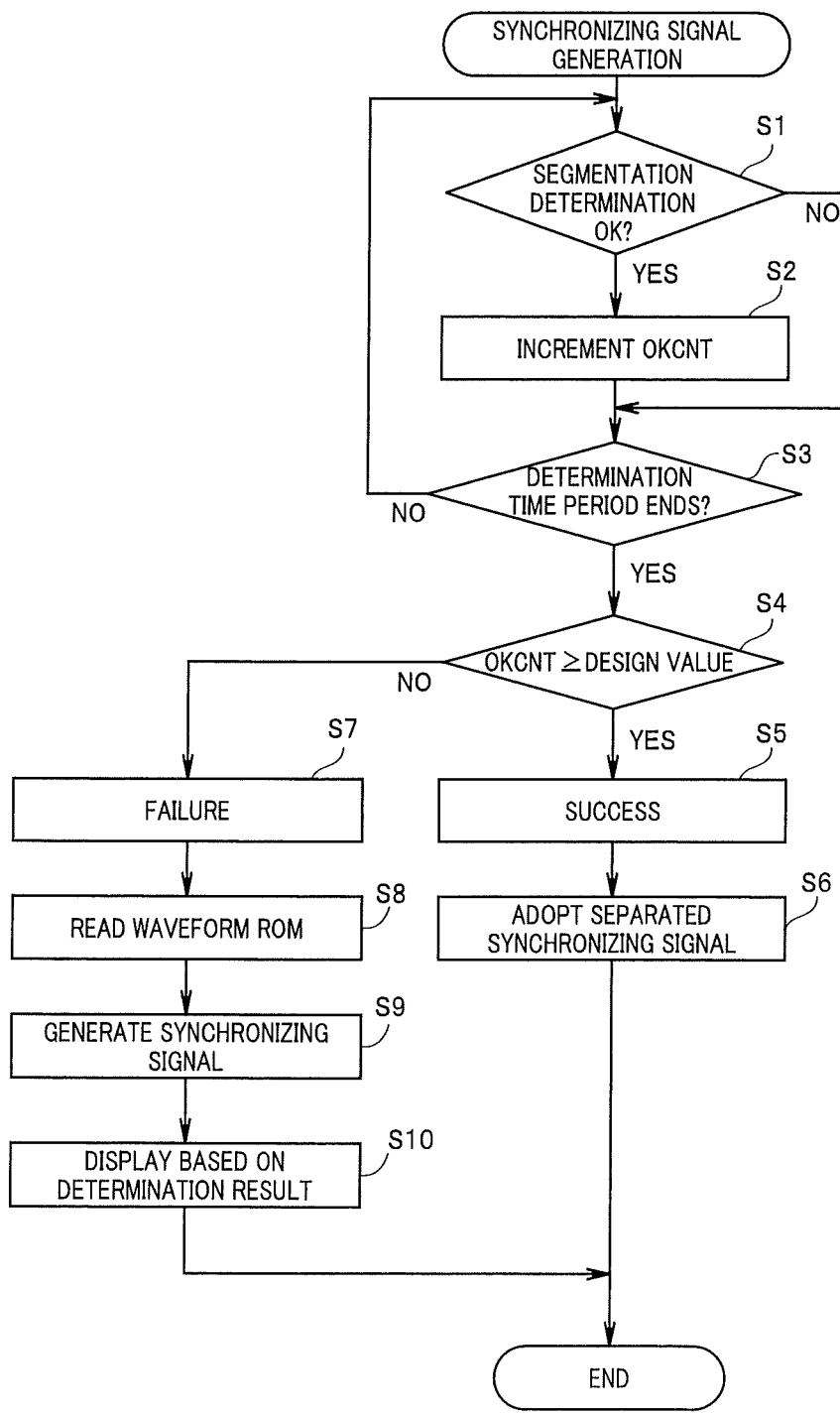
FIG. 5 is a flowchart for explaining an operation of the embodiment.
Figure 6:
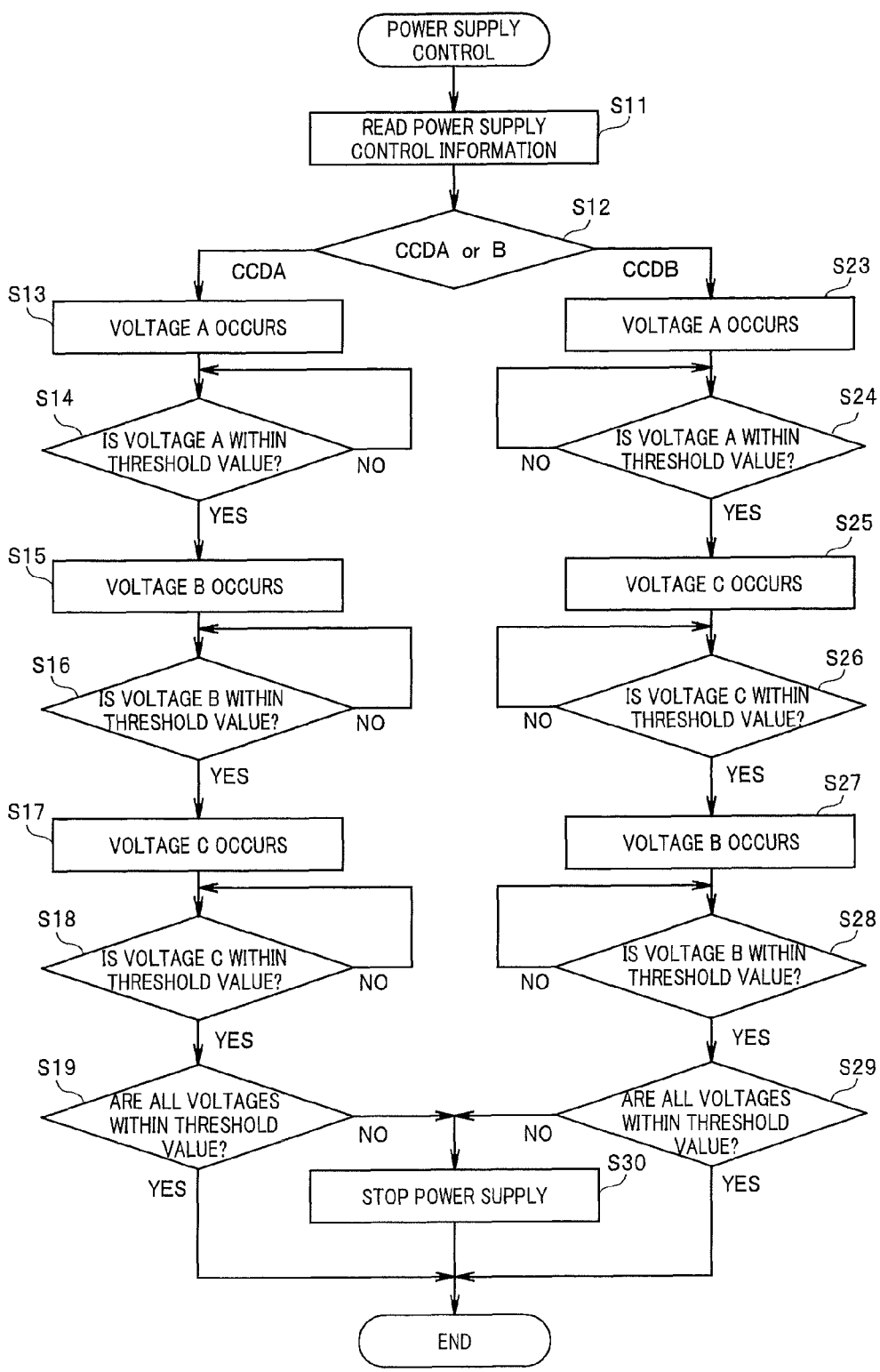
FIG. 6 is a flowchart for explaining an operation of the embodiment.

Next, an operation of the embodiment which is configured as above will be described with reference to flowcharts of FIGS. 5 and 6. FIG. 5 shows synchronizing signal generation processing in the FPGA 17 in FIG. 1. Further, FIG. 6 shows power supply control by the FPGA 17.

The connector 4 of the scope cable 5 is connected to the scope 1, and the connector 6 is connected to the connector 12 of the video processor 10. Thereby, the CPU section 22 reads the scope information stored in the ROM 3 of the scope 1. The scope information is also given to the FPGA 17. Further, the CCD detection signal based on the resistance value of the detection resistor 7 is supplied to the FPGA 17. The FPGA 17 outputs the CCD detection signal to the CPU section 22.

The CPU section 22 controls the clock generating section 23 to generate CTLCLK. The FPGA 17 can receive the CCD detection signal by using the CTLCLK. When the FPGA 17 detects that an undetectable, undrivable and non-associated CCD is connected by the CCD detection signal, the FPGA 17 outputs the determination information indicating that such a CCD is connected to the CPU section 22, and causes the drive section 13 to stop power supply to the scope 1. The determination information is stored in the error storing section 27 by the CPU section 22. Further, the CPU section 22 controls the OSD processing section 26a, and causes the OSD processing section 26a to display the message indicating that the undetectable, undrivable and non-associated CCD is connected, on the screen of the monitor 41.

Thereby, a user can be reliably notified that a non-associated CCD is connected, and can be reliably notified of a failure of the scope and the like. Further, by stop of power supply to the scope, breakage of the scope is likely to be able to be prevented. Further, by storing the determination information in the error storing section 27, quick repair or the like can be enabled.

When a drivable CCD is connected, the CPU section 22 grasps the kind of the CCD by the CCD detection signal, and controls the clock generating section 23 to generate a clock suitable for the CCD 2. Thereby, the clock generating section 23 generates a reference CLK and supplies the reference CLK to the FPGA 17. Further, the clock generating section 23 generates VDCLK and outputs the VDCLK to the FPGA 17.

The FPGA 17 generates a timing signal including various clocks correspondingly to the reference clock and supplies the timing signal to the drive section 13, and supplies the VDCLK to the drive section 13. The drive section 13 generates a drive signal by using the inputted timing signal, and superimposes the synchronizing signal based on the VDCLK on the drive signal. The drive signal from the drive section 13 is supplied to the CCD 2 of the scope 1 through the scope cable 5.

Further, the FPGA 17 reads the power supply control information corresponding to the kind of the CCD from the information storing section 18, generates a power supply control signal based on the power supply control information and controls the power supply section 13a. For example, it is assumed that a CCD A or a CCD B is connectable to the video processor 10 now, the CCD A is normally operated by being supplied with a power in the sequence of voltages A, B and C, and the CCD B is normally operated by being supplied with a power in the sequence of voltages A, C and B.

The FPGA 17 reads the power supply control information based on the CCD detection signal from the information storing section 18, in step S11 of FIG. 6. For example, it is assumed that the CCD detection signal indicates that the CCD A is connected as the CCD 2. In this case, the FPGA 17 shifts the processing from step S12 to step S13, and causes the power supply section 13a to generate a voltage A by a power supply control signal. The power supply section 13a generates the voltage A, and the voltage A is converted into a digital signal to be fed back to the FPGA 17 by the power supply monitoring section 19. The FPGA 17 determines whether or not the voltage based on the output of the information storing section 18 is within the range of the lower limit threshold voltage of the voltage A (within the threshold value) (step S14). For example, as the lower limit threshold value, the voltage of 80% of a rated voltage is set.

When the FPGA 17 determines that the voltage A reaches the lower limit threshold value, the FPGA 17 generates a power supply control signal for generating a voltage B in the next step S15. Hereinafter, in the same manner, the voltage B reaches the lower limit threshold value of the voltage B, whereby the voltage C is generated (steps S16 and S17), and the voltage C reaches the lower limit threshold value (step S18), whereby the processing shifts to step S19. In step S19, it is determined whether or not all the voltages are within the range of the upper limit threshold voltage (within the threshold value). For example, as the upper limit threshold value, the voltage of 120% of the rated voltage is set.

Similarly, when it is indicated that the CCD B is connected as the CCD 2 by the CCD detection signal, the FPGA 17 sequentially generates the voltages A, C and B by the processing of steps S23 to S38. When all the voltages to be supplied to each CCD are not the voltages between the lower limit threshold value and the upper limit threshold value in steps S19 and S29, the processing is shifted to step S30, and power supply is stopped.

In FIG. 6, when at the time of generation of each of the voltages, the voltage does not reach the lower limit threshold value even after a predetermined time or a longer time elapses, the processing is shifted to step S30, and power supply may be stopped.

As above, in the present embodiment, in the FPGA 17, the voltage corresponding to the kind of the CCD can be successively generated in the sequence corresponding to the kind of the CCD. Further, the FPGA 17 can stop voltage supply under abnormal conditions by monitoring the generated voltage.

Further, the FPGA 17 also detects an overcurrent of the power supply current from the power supply section 13a. The power supply monitoring section 19 converts the power supply current into a digital value by sampling the power supply current. The FPGA 17 determines whether or not an overcurrent is generated based on an average value of the current values obtained by sampling of twice or more times of the power supply monitoring section 19.

For example, the power supply monitoring section 19 performs A/D conversion of the power supply current which is supplied from the power supply section 13a to the CCD 2 with a sampling period of 200 Hz. The FPGA 17 obtains a moving average of the most recent four sampled current values at each sampling of the power supply monitoring section 19. When the sampled current value is 150 mA or more, the moving average is calculated with the current upper limit value as 150 mA. When the calculated moving average value exceeds 130 mA which is the detection threshold value successively three times, it is determined that an overcurrent flows. When determining that an overcurrent flows, the FPGA 17 stops the power supply of the power supply section 13a, for example.

The sampling period, the number of times of sampling used in the moving average, the current upper limit value and the detection threshold value are not limited to the numeric values shown here.

When the power supply is normally supplied, the CCD 2 performs photoelectric conversion of a subject optical image, and outputs the accumulated charges of each pixel as an image pickup signal in accordance with the drive signal from the drive section 13. In this case, the CCD 2 outputs the image pickup signal on which a synchronizing signal is imposed at timing corresponding to the OB section. The image pickup signal from the CCD 2 is supplied to the synchronizing signal processing section 14 and the preamplifier section 15 of the video processor 10 through the scope cable 5.

The preamplifier section 15 amplifies the inputted image pickup signal, and the analog processing section 16 applies CDS processing and A/D conversion processing to the amplified image pickup signal, and outputs the digital image pickup signal to the FPGA 17.

Meanwhile, the FPGA 17 reads the information of a delay time from the information storing section 18 based on the CCD detection signal and the scope information. The FPGA 17 generates a gate signal based on the read information, and outputs the gate signal to the synchronizing signal processing section 14.

The synchronizing signal processing section 14 compares the inputted image pickup signal with the reference potential and generates a timing signal, and outputs the timing signal in the gate time period which is specified by the gate signal as a synchronizing signal. The synchronizing signal is supplied to the FPGA 17.

In the present embodiment, the FPGA 17 determines whether or not the synchronizing signal from the synchronizing signal processing section 14 is normal. For example, the FPGA 17 sets a predetermined determination time period, and determines whether or not the synchronizing signal is normal based on how many times the synchronizing signal processing section 14 can separate the synchronizing signal within the determination time period. The FPGA 17 determines whether segmentation determination that indicates that the synchronizing signal can be separated in the synchronizing signal processing section 14 is OK or not in step S1 of FIG. 5. Only when the segmentation determination is OK, a variable OKCNT is incremented (step S2).

The FPGA 17 determines whether or not the determination time period ends in step S3. Steps S1 to S3 are repeated, and it is determined how many times the segmentation determination becomes OK during the determination time period. In the next step S4, the FPGA 17 determines whether or not the variable OKCNT becomes a design value or larger (step S4). When the variable OKCNT is the design value or larger, the FPGA 17 determines that the FPGA 17 succeeds in separation of the synchronizing signal in the next step S5, and adopts the separated synchronizing signal in step S6 to perform the following processing.

Meanwhile, when the variable OKCNT is smaller than the design value, the FPGA 17 determines that the FPGA 17 fails in separation of the synchronizing signal in the next step S7, and reads the information of a delay time from the information storing section 18 in step S8. The FPGA 17 generates a synchronizing signal by counting the reference CLK based on the information of the delay time with the VDCLK as a reference (step S9). Thereafter, the FPGA 17 adopts the generated synchronizing signal and performs the following processing.

As above, it is determined whether or not the synchronizing signal from the synchronizing signal processing section 14 is normal based on whether or not the number of times of success in synchronizing signal separation during the predetermined determination time period reaches the design value, instead of determination of one time, and erroneous detection can be prevented.

The FPGA 17 converts an image pickup signal into the R, G and B video signals, multiplexes a separated or generated synchronizing signal onto the R, G and B video signals, and transmits the R, G and B video signals to the R, G and B signal processing sections 24R, 24G and 24B by using the LVDS. The R, G and B signal processing sections 24R, 24G and 24B perform signal processing to the R, G and B video signals, and the matrix section 25 performs matrix processing to the outputs of the R, G and B signal processing sections 24R, 24G and 24B. The R, G and B video signals from the matrix section 25 are supplied to the monitor 41, after the image processing section 26 applies γ correction processing, white balance adjustment processing and the like to the R, G and B video signals. Thus, image display based on the picked up image of the CCD 2 is performed on the display screen of the monitor 41.

Meanwhile, when the synchronizing signal is not separated normally in the synchronizing signal processing section 14, the FPGA 17 outputs the determination information indicating that the synchronizing signal is not separated normally in the synchronizing signal processing section 14 to the CPU section 22. The CPU section 22 controls the OSD processing section 26a, and causes the OSD processing section 26a to superimpose the display indicating that the synchronizing signal is not separated normally in the synchronizing signal processing section 14, on the endoscopic image. For example, the display indicating that separation of the synchronizing signal is not performed normally, the display pointing out a contact failure of the cable or the like can be made on the screen of the monitor 41.

In the present embodiment, the processing of FIG. 5 is performed in the predetermined time period immediately after power supply is turned on, but the processing of FIG. 5 may be carried out at predetermined timing except for immediately after the power supply is turned on.

As above, in the present embodiment, when it is determined that the synchronizing signal cannot be separated normally, the information of the delay time is read from the information storing section, whereby the synchronizing signal is generated and used in the following processing. Thereby, even when a failure, aged deterioration, a contact failure or the like of the transmission path characteristic of the scope occurs, and the synchronizing signal cannot be separated, the synchronizing signal is generated, video processing is enabled, and a picked up image can be projected.

Further, in the present embodiment, in the information storing section, data corresponding to the kind of the CCD and the kind of the scope cable is retained, and when any kinds of scope and CCD are connected to the video processor, a synchronizing signal can be reliably generated.

In the above described embodiment, the example is described, in which the CCD outputs the image pickup signal on which a synchronizing signal is superimposed, and the synchronizing signal superimposed on the image pickup signal is separated in the synchronizing signal processing section, but the present invention is similarly applicable to the example in which the CCD outputs an image pickup signal including a synchronizing signal, and the synchronizing signal included in the image pickup signal is detected in the synchronizing signal processing section.

What is claimed is:

1. An endoscopic image processing apparatus, comprising:
an endoscope information reading section that reads endoscope information that is information relating to an endoscope from the endoscope;
a synchronizing signal detecting section that is given an image pickup signal that includes a synchronizing signal outputted by an image pickup device provided in the endoscope from the endoscope, performs detection processing of the synchronizing signal, outputs the detected synchronizing signal when the synchronizing signal can be detected, and generates and outputs a synchronizing signal based on the endoscope information read by the endoscope information reading section when the synchronizing signal cannot be detected; and
an image signal generating section that generates an image signal based on the synchronizing signal outputted from the synchronizing signal detecting section and the image pickup signal outputted from the image pickup device of the endoscope.

2. The endoscopic image processing apparatus according to claim 1,
wherein the synchronizing signal detecting section detects the synchronizing signal superimposed on the image pickup signal by a synchronizing signal separating section that separates the synchronizing signal from the image pickup signal, when the synchronizing signal is superimposed on the image pickup signal.

3. The endoscopic image processing apparatus according to claim 2,
wherein the synchronizing signal detecting section determines whether or not the synchronizing signal separating section succeeds in detection of the synchronizing signal according to a number of times in which the synchronizing signal is separable within a predetermined determination time period.

4. The endoscopic image processing apparatus according to claim 1, comprising an image processing section that performs image processing with respect to the image signal generated by the image signal generating section,
wherein when the synchronizing signal included in the image pickup signal cannot be detected in the synchronizing signal detecting section, the image processing section superimposes information indicating that the synchronizing signal included in the image pickup signal cannot be detected in the synchronizing signal detecting section on the image signal.

5. The endoscopic image processing apparatus according to claim 1, further comprising:
an image pickup device drive section that outputs power supply and a drive signal for driving the image pickup device;
an image pickup device information reading section that reads image pickup device information that is information relating to the image pickup device from the endoscope; and
a control section that controls the image pickup device drive section to stop output of the power supply and the drive signal to the image pickup device when the image pickup device information reading section cannot read the image pickup device information about the image pickup device that can be driven in the image pickup device drive section.

6. The endoscopic image processing apparatus according to claim 5, comprising an image processing section that performs image processing with respect to the image signal generated by the image signal generating section,
wherein when the image pickup device information reading section cannot read the image pickup device information about the image pickup device that can be driven in the image pickup device drive section, the image processing section superimposes information indicating that the image pickup device information reading section cannot read the image pickup device information about the image pickup device which can be driven in the image pickup device drive section on the image signal.

7. An endoscope system comprising an endoscope and a video processor connected to the endoscope,
wherein the endoscope comprises
an image pickup device that picks up an image of a subject, and outputs an image pickup signal including a synchronizing signal, and
a storing section that stores endoscope information that is information relating to the endoscope; and
the video processor comprises
an endoscope information reading section that reads the endoscope information from the endoscope,
a synchronizing signal detecting section that is given an image pickup signal that includes a synchronizing signal outputted by the image pickup device from the endoscope, performs detection processing of the synchronizing signal, outputs the detected synchronizing signal when the synchronizing signal can be detected, and generates and outputs a synchronizing signal based on the endoscope information read by the endoscope information reading section when the synchronizing signal cannot be detected, and
an image signal generating section that generates an image signal based on the synchronizing signal outputted from the synchronizing signal detecting section and the image pickup signal outputted from the image pickup device of the endoscope.

8. The endoscope system according to claim 7,
wherein the image pickup device outputs the synchronizing signal by superimposing the synchronizing signal on the image pickup signal, and
the synchronizing signal detecting section detects the synchronizing signal superimposed on the image pickup signal by a synchronizing signal separating section that separates the synchronizing signal from the image pickup signal.

9. The endoscope system according to claim 8,
wherein the synchronizing signal detecting section determines whether or not the synchronizing signal separating section succeeds in detection of the synchronizing signal according to a number of times in which the synchronizing signal is separable within a predetermined determination time period.

10. The endoscope system according to claim 7,
wherein the video processor comprises an image processing section that performs image processing with respect to the image signal generated by the image signal generating section, and when the synchronizing signal included in the image pickup signal cannot be detected in the synchronizing signal detecting section, the image processing section superimposes information indicating that the synchronizing signal included in the image pickup signal cannot be detected in the synchronizing signal detecting section on the image signal.

11. The endoscope system according to claim 7,
wherein the endoscope has an image pickup device storing section that stores image pickup device information that is information relating to the image pickup device, and
the video processor comprises
an image pickup device drive section that outputs power supply and a drive signal for driving the image pickup device,
an image pickup device information reading section that reads the image pickup device information from the endoscope, and
a control section that controls the image pickup device drive section to stop output of the power supply and the drive signal to the image pickup device, when the image pickup device information reading section cannot read the image pickup device information about the image pickup device which can be driven in the image pickup device drive section.

12. The endoscope system according to claim 11,
wherein the video processor comprises an image processing section that performs image processing with respect to the image signal generated by the image signal generating section, and
when the image pickup device information reading section cannot read the image pickup device information about the image pickup device that can be driven in the image pickup device drive section, the image processing section superimposes information indicating that the image pickup device information reading section cannot read the image pickup device information about the image pickup device which can be driven in the image pickup device drive section on the image signal.

\* \* \* \* \*